(12) United States Patent
McGregor

(10) Patent No.: US 11,119,024 B2
(45) Date of Patent: Sep. 14, 2021

(54) METHOD AND APPARATUS FOR MEASURING PERMEABILITY IN THE DIRECTION OF PRESSURE GRADIENT

(71) Applicant: Halliburton Energy Services, Inc., Houston, TX (US)

(72) Inventor: Jacob Andrew McGregor, Fort Worth, TX (US)

(73) Assignee: Halliburton Energy Services, Inc., Houston, TX (US)

(*) Notice: Subject to any disclaimer, the term of this patent is extended or adjusted under 35 U.S.C. 154(b) by 82 days.

(21) Appl. No.: 16/582,276

(22) Filed: Sep. 25, 2019

(65) Prior Publication Data

US 2021/0088434 A1    Mar. 25, 2021

(51) Int. Cl.
*G01N 15/08* (2006.01)
*G01N 33/24* (2006.01)
*E21B 49/02* (2006.01)

(52) U.S. Cl.
CPC ......... *G01N 15/0826* (2013.01); *E21B 49/02* (2013.01); *G01N 15/0806* (2013.01)

(58) Field of Classification Search
CPC .... G01N 15/00; G01N 15/08; G01N 15/0806; G01N 15/0826; G01N 33/24; E21B 49/00–02
See application file for complete search history.

(56) References Cited

U.S. PATENT DOCUMENTS

| 2,345,935 A | 4/1944 | Hassler |
| 2010/0268488 A1 | 10/2010 | Bismarck et al. |
| 2018/0335374 A1* | 11/2018 | Kanj ................. G01N 15/0826 |
| 2019/0391065 A1* | 12/2019 | Karazincir ............ G01N 33/24 |

FOREIGN PATENT DOCUMENTS

| DE | 69733507 T2 | 5/2006 |
| DE | 112017007817 T5 | 4/2020 |

OTHER PUBLICATIONS

Hassler, G. L., et al., "Investigations on the Recovery of Oil from Sandstones by Gas Drive," New York Meeting, Feb. 1936, pp. 116-137.

* cited by examiner

*Primary Examiner* — Nguyen Q. Ha
(74) *Attorney, Agent, or Firm* — John Wustenberg; Parker Justiss, P.C.

(57) ABSTRACT

Provided herein are embodiments of a method and apparatus for measuring permeability of a rock core sample in the direction of pressure gradient. In one embodiment, a method includes providing a rock core sample having an inlet primary face, an outlet primary face and one or more sidewalls having a thickness (T) adjoining the inlet and outlet primary face, wherein the inlet primary face has a surface area ($SA_{IF}$) and the one or more sidewalls have a surface area ($SA_{SW}$), and further wherein a ratio of the inlet primary face surface area ($SA_{IF}$) to sidewall surface area ($SA_{SW}$) is at least 0.4; placing the rock core sample, unbounded, between an inlet flow plate and an outlet flow plate; directing a fluid through from the inlet flow plate into the rock core sample; and measuring a flow rate of the fluid exiting the outlet flow plate.

20 Claims, 3 Drawing Sheets

METHOD AND APPARATUS FOR MEASURING PERMEABILITY IN THE DIRECTION OF PRESSURE GRADIENT

BACKGROUND

In order to predict a well's production, plan for well construction, and among other things, design a perforation tool and/or a downhole perforation procedure, one or more rock core samples that are considered to be representative of the subterranean formation may be tested in a laboratory setting. As those skilled in the art appreciate, such testing assists in determining certain parameters of the subterranean formation and/or interactions between the explosive charges and the subterranean formation. The test results may then be used in designing the wellbore perforation tool and/or the downhole perforation procedure.

BRIEF DESCRIPTION

Reference is now made to the following descriptions taken in conjunction with the accompanying drawings, in which.

DETAILED DESCRIPTION

Figure 1:
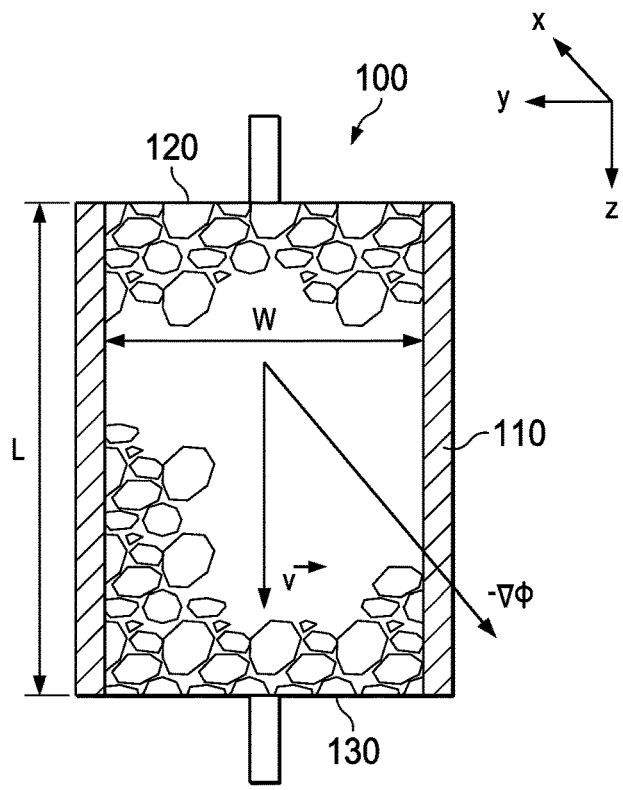
FIG. 1 represents a traditional method for testing permeability of a rock core sample.

Although illustrative implementations of one or more embodiments are discussed below, the disclosed systems and methods may be implemented using any number of techniques, whether currently known or in existence. The disclosure should in no way be limited to the illustrative implementations, drawings, and techniques shown below, but may be modified within the scope of the appended claims along with their full scope of equivalents.

Permeability (K) is a measure of a porous material's ability to allow fluids to pass through the porous material. Permeability (K) may be measured, for instance, in darcies (d) or millidarcies (md). For example, a material has a permeability of 1 darcy (d) if through a face of one square centimeter, which is normal to the direction of flow, one milliliter per second of fluid passes through the material. A porous medium has an absolute permeability of one darcy when a single-phase fluid of one centipoise viscosity that completely fills the voids of the medium will flow through it under conditions of viscous flow at a rate of 1 cm$^3$/s per 1 cm$^2$ bulk cross-sectional area under a pressure or equivalent fluid potential gradient of one atmosphere per centimeter. Directional permeability is of great importance in reservoir fluid flow, whose flow is three-dimensional. The present disclosure has recognized that the accurate measurement of a rock core sample's permeability in the direction of pressure gradient is significant in various stages of well planning and preparation, including but not limited to forecasting well performance and construction and completion planning for a well. Embodiments will be discussed herein which provide for measuring a rock core sample's permeability in the direction of the pressure gradient.

Testing of rock core samples may be conducted to evaluate reservoir fluid flow. Testing is typically performed on a rock core sample that is considered to be representative of the subterranean formation. For example, cuttings from a subterranean formation retrieved from the wellbore may be captured and analyzed to determine characteristics of the rock of the subterranean formation. An outcrop rock core sample is selected based on the similarity of its characteristics to the characteristics of the cuttings from the subterranean formation. The outcrop rock core sample may be trimmed to be suitable for core testing. Rock core samples taken for measuring permeability have been cut, in some examples, in a generally circular cylinder form about 18 centimeters (e.g., a little over 7 inches) in diameter (D) and about 70 centimeters (e.g., a little over 27 inches) in axial length (L), in one example. The one or more sidewalls of the rock core sample are then traditionally bound, and the permeability is measured by maintaining a constant fluid potential difference across the rock core sample's primary ends. However, this traditional method of measuring permeability of a rock core sample provides only a two-dimensional (e.g., along a single direction) measurement, providing only the permeability in the direction of flow.

One example of a traditional rock core sample and permeability test is shown in FIG. 1. In this example, a rock core sample 100 is cut into a relatively long and narrow cylinder shape having a width (W) and a length (L), wherein a ratio of width (W) to length (L) is much less than 1 (W/L<<1). The rock core sample is then bound by applying a no-flow boundary, such as a sleeve 110, about the rock core sample's 100 sidewalls (e.g., cylindrical surface). The permeability of the rock core sample 100, now bound, is measured by maintaining a constant fluid potential difference across its primary ends 120 and 130. In the example shown in FIG. 1, as a result of the sleeve 110, a flow velocity vector $\vec{v}$ must be compelled along a vertical axis (z) of the rock core sample. However, with such boundaries, and due to the tensorial nature of permeability, a potential gradient is, in general oblique, neither perpendicular nor parallel to the rock core sample's 100 vertical axis (z), yielding a value for permeability in the direction of flow and not in a direction of potential (e.g., pressure) gradient.

Figure 2:
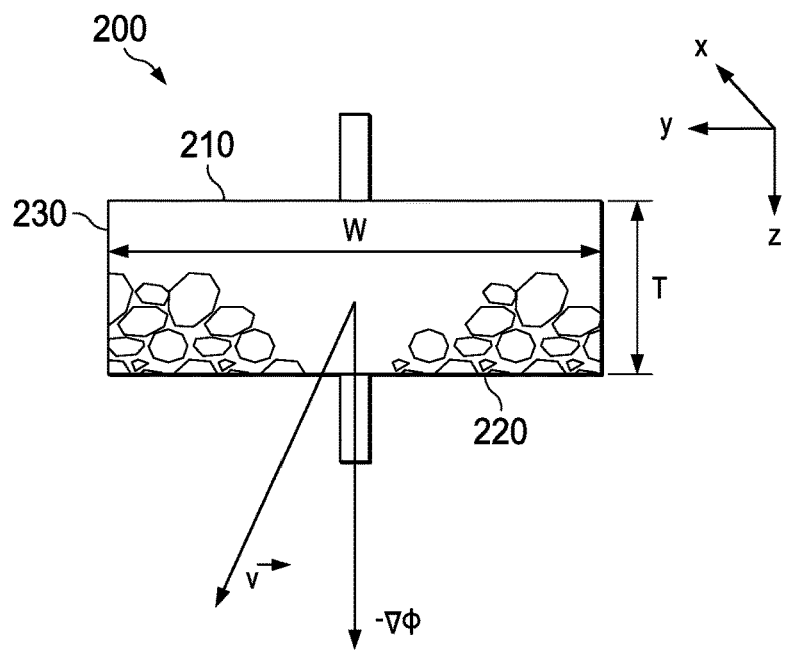
FIG. 2 represents one embodiment of a method for testing permeability of a rock core sample according to principles of the disclosure.

Referring now to FIG. 2, there is shown one embodiment of a rock core sample 200 according to the disclosure, illustrating one example for determining permeability in a direction of a pressure gradient according to the disclosure. In this example, the rock core sample 200 may be cut into a shape having an inlet primary face 210 and an outlet primary face 220. The inlet primary face 210 and outlet primary face 220, in the illustrated embodiment, are separated by one or more sidewalls 230. The rock core sample illustrated in FIG. 2 thus has a thickness (T) and a width (W). The inlet primary face 210 may have a surface area ($SA_{IF}$), the one or more sidewalls 230 may have a surface area ($SA_{SW}$), and the outlet primary face 220 may have a surface area ($SA_{OF}$). In accordance with one embodiment of the disclosure, a ratio of the inlet primary face 210 surface area ($SA_{IF}$) to the sidewall 230 surface area ($SA_{SW}$) is at least 0.4. For example, in one embodiment, the inlet primary face surface area ($SA_{IF}$) may be about 5.067 cm$^2$ and the sidewall surface area ($SA_{SW}$) may be about 10.135 cm$^2$ and the ratio is about 0.499. In other embodiments, the ratio may be at least 1, and in some embodiments, the ratio may be greater than about 1.75. The ratio may increase as the size, (e.g. diameter) of the inlet primary face is bigger. For example, in some embodiments, the ratio may be greater than about 3.5, and in still other embodiments, the ratio may range from about 3.5 and 6. In accordance with another embodiment, particularly when the rock core sample 200 is a cylinder having a diameter (D), a ratio of the diameter (D) to the thickness (T) is greater than 1, and in some instances greater than 2.

In some embodiments, the inlet primary face 210 and the outlet primary face 220 may be substantially parallel equipotential plane boundaries, as shown. The term substantially parallel, as used in this paragraph, means that the inlet primary face 210 and the outlet primary face 220 are within about 10 degrees from perfectly parallel. Other embodiments may exist wherein one or both of the inlet primary face 210 and the outlet primary face 220 are ideally parallel, which means that one or both of the inlet primary face 210 and the outlet primary face 220 are within about 5 degrees from perfectly parallel.

In this embodiment, maintaining a constant fluid potential difference across the inlet primary face 210 and the outlet primary face 220 may allow fluid to flow along the z axis. In this example, a fluid potential gradient vector $-\nabla\Phi$ may be substantially perpendicular to at least one of the inlet primary face 210 or the outlet primary face 220. In some embodiments, the inlet primary face 210 and the outlet primary face 220 may be equipotential surfaces (or isopotential surfaces having a constant $\Phi$) and the fluid potential gradient vector $-\nabla\Phi$ may be substantially perpendicular to the equipotential surfaces. A velocity vector if $\vec{v}$ may be generally oblique, neither perpendicular nor parallel, to the equipotential surfaces (e.g., the inlet primary face 210 and the outlet primary face 220) and inclined to a principal axes of permeability such that fluid may move in a direction of least resistance). As used within this paragraph, substantially perpendicular means that two surfaces are within 10 degrees of perfectly perpendicular from each other. For example, the fluid potential gradient vector $-\nabla\Phi$ may be substantially perpendicular to the equipotential surfaces when the fluid potential gradient vector $-\nabla\Phi$ is within 10 degrees of perfectly perpendicular to the equipotential surfaces (e.g., the inlet primary face 210 and the outlet primary face 220).

In this embodiment, the rock core sample 200 is unbounded, meaning the one or more sidewalls 230 are not insulated or surrounded by a component such as, e.g., a sleeve. The rock core sample 200 being unbounded, or uninsulated, enables fluid to exit both the one or more sidewalls 230, and the outlet primary face 220. The fluid exiting the outlet primary face 220 may then be measured, which may be used in measuring permeability according to the disclosure. In accordance with this disclosure, the measured permeability may yield a value for the permeability of the rock core sample 200 in the direction of the potential (e.g. pressure) gradient. The fluid used can be any type of fluid, e.g., liquid, gas, or multiple phases, e.g., both liquid and gas, or two distinct liquids such as oil and water. If the one or more sidewalls 230 were made to be bounded (e.g., a "no-flow boundary", as is commonly done) the components of the flow vector [$\vec{v}$(vx,vy, vz)] in the transverse directions will be diverted in an axial direction and included in the flow measurement. Accordingly, the ratio of the total flow (e.g., in all directions) to the pressure drop (e.g., in a direction along the z axis) would be computed, instead of the permeability of the rock core sample 200 in the direction of the potential (e.g. pressure) gradient.

Embodiments disclosed herein may use a rock core sample 200 cut into various different geometries. For example, although the example shown in FIG. 2 is a cylindrical or wafer-like shape, other embodiments may include rock core samples 200 that are not cylindrical, such as cuboids, etc.

Figure 3A:
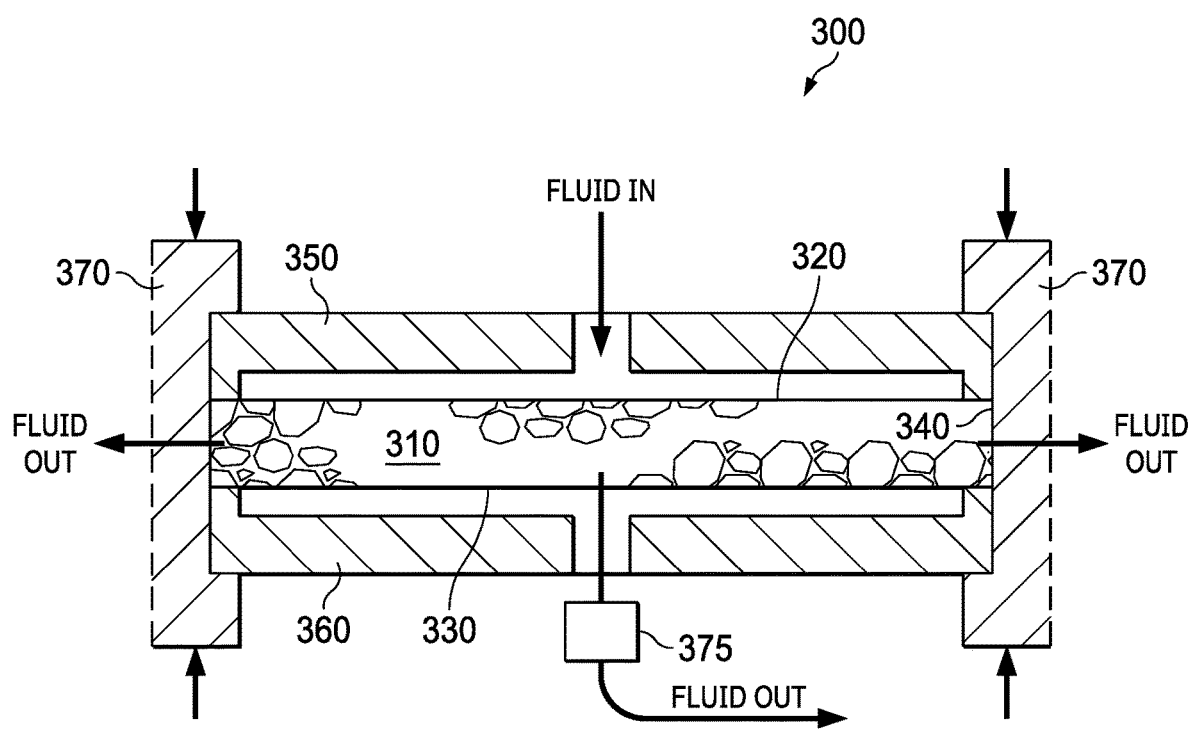
FIG. 3A illustrates one embodiment of a testing apparatus for testing permeability of a rock core sample according to principles of the disclosure.

"Referring now to FIG. 3A, shown is a testing apparatus 300 which may be used to measure permeability of a rock core sample 310 according to one or more embodiments of the present disclosure. The rock core sample 310 may include an inlet primary face 320, an outlet primary face 330, and one or more sidewalls 340. The testing apparatus 300, in this embodiment, includes an inlet flow distributor plate 350 and an outlet flow distributor plate 360. One or more rods 370, may be coupled with or clamped about the inlet flow distributor plate 350, rock core sample 310, and the outlet flow distributor plate 360. While the one or more rods may be designed to maintain constant contact between the rock core sample 310 and the inlet and outlet flow distributor plates 350 and 360 through the duration of the permeability test, the one or more rods should not prevent fluid from exiting the sidewalls 340 of the rock core sample 310 during the permeability test. In this example, the rods 370 are not threaded, but the rods 370 may be threaded rods in other embodiments. In some embodiments the inlet flow plate 350 may include a first pressure transducer coupled thereto. In another embodiment, the outlet flow plate 360 may include a second pressure transducer coupled thereto, wherein the first and second pressure transducers translate the fluid pressure across the inlet flow plate 350 and outlet flow plate 360 into an electrical signal."

In some embodiments, the inlet and outlet flow plates 350, 360 may form equipotential boundaries about the inlet primary face 320 and the outlet primary face 330 of the rock core sample 310. In this embodiment, the rock core sample 310 is placed between the inlet flow plate 350 and outlet flow plate 360 unbound, meaning not insulated or bound by any sleeve, insulation, or similar structure. Fluid may be directed through the inlet flow plate 350 from an incoming pump. The inlet flow plate 350 may then distribute the fluid across the inlet primary face 320 of the rock core sample 310. The fluid then flows through the rock core sample 310 and may exit the rock core sample 310 through one or more of the sidewalls 340 and through the outlet primary face 330. A flow meter 375 may be placed proximate the outlet primary face 330 to measure fluid exiting from the outlet primary face 330 of the rock core sample 310, for example to calculate the permeability of the rock core sample. In some embodiments, the flow meter 375 may be placed adjacent the outlet flow plate 360.

Figure 3B:
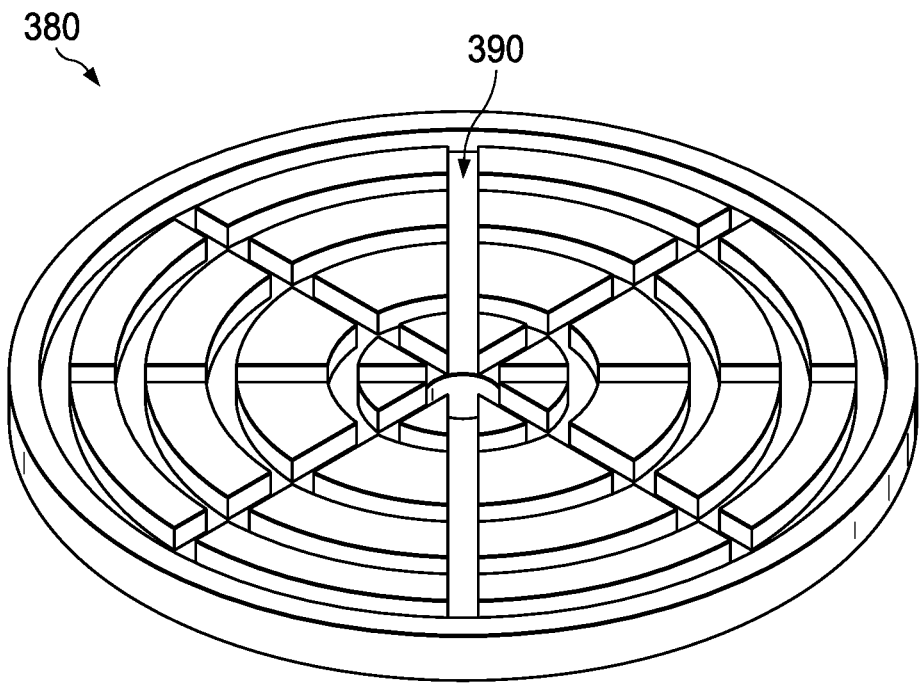
FIG. 3B illustrates one embodiment of one component of the testing apparatus shown in FIG. 3A for testing permeability of a rock core sample according to principles of the disclosure.

One embodiment of a flow distributor plate 380, which may be used as either the inlet flow plate 350, the outlet flow plate 360, or both the inlet flow plate 350 and outlet flow plate 360, is shown in FIG. 3B. The flow distributor plate 380 may include a plurality of distribution channels 390 for distributing fluid across the inlet primary face 320, and collecting fluid from the outlet primary face 330, of the rock core sample 310. In some embodiments, the distribution channels 390 may include a plurality of concentric, axial rings, connected by one or more radial paths.

Figure 4:
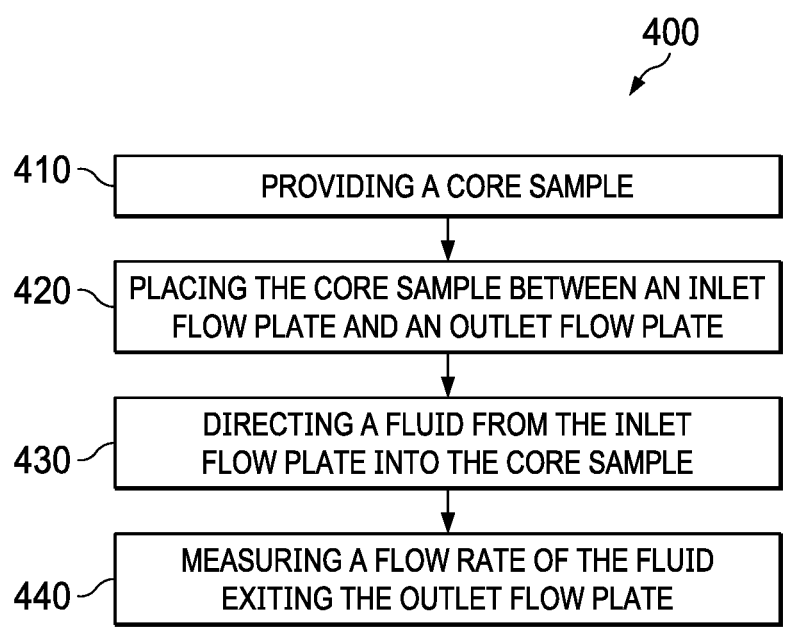
FIG. 4 illustrates one method for testing permeability of a rock core sample in accordance with one embodiment of the disclosure.

Referring now to FIG. 4, there is a flowchart illustrating steps of one method 400 for determining permeability of a rock core sample, such as rock core sample 200, according to the disclosure. In a step 410, the method 400 includes providing a rock core sample obtained from a porous medium. In one embodiment, the rock core sample may have an inlet primary face, an outlet primary face and one or more sidewalls having a thickness (T) adjoining the inlet primary face and the outlet primary face. In some embodiments, the inlet primary face may have a surface area ($SA_{IF}$), the one or more sidewalls may have a surface area ($SA_{SW}$), and the outlet primary face may have a surface area ($SA_{OF}$). In this example, a ratio of the inlet primary face surface area ($SA_{IF}$) to sidewall surface area ($SA_{SW}$) is at least 0.4, but other ratios (e.g., those discussed above) may also be used and remain within the purview of the disclosure.

In a next step 420, the rock core sample is placed, unbounded, between an inlet flow plate, coupled to the inlet primary face, and an outlet flow plate, coupled to the outlet primary face. In a next step 430, fluid is directed from the inlet flow plate into the rock core sample. In a next step 440, a flow rate of fluid exiting the outlet flow plate in measured. As discussed above, the flow rate of the fluid exiting the outlet flow plate may be used to calculate the permeability of the rock core sample in the direction of the potential (e.g. pressure) gradient.

Aspects disclosed herein include: A. A method for testing permeability. The method, in one embodiment, comprising directing fluid through a rock core sample having an inlet primary face, an outlet primary face and one or more sidewalls having a thickness (T) adjoining the inlet primary face and the outlet primary face, the directing occurring while the sidewalls are unbounded; and measuring a flow rate of fluid exiting the outlet primary face.

Aspect A may have one or more of the following additional elements in combination: Element 1: wherein directing fluid through a rock core sample includes directing fluid through a rock core sample having a ratio of an inlet primary face surface area ($SA_{IF}$) to a sidewall surface area ($SA_{SW}$) of at least about 0.4. Element 2: further including placing the rock core sample between an inlet flow plate coupled to the inlet primary face and an outlet flow plate coupled to the outlet primary face prior to directing fluid through the rock core sample. Element 3: further including forming equipotential boundaries on the inlet primary face and the outlet primary face using the inlet and outlet flow plates. Element 4, further including creating a fluid potential gradient vector within 10 degrees of perpendicular with the equipotential boundaries. Element 5: further including directing fluid through a plurality of distribution channels in the inlet flow plate. Element 6: further including directing fluid through a plurality of concentric axial rings in the inlet flow plate. Element 7: further including directing fluid through the plurality of concentric axial rings connected by one or more radial paths in the inlet flow plate. Element 8: further including collecting fluid from a plurality of distribution channels in the outlet flow plate. Element 9: further including collecting fluid from a plurality of concentric axial rings in the outlet flow plate. Element 10: further including collecting fluid from the plurality of concentric axial rings connected by one or more radial paths in the outlet flow plate. Element 11: further including translating a first fluid pressure across the inlet flow plate using a first pressure transducer. Element 12: further including translating a second pressure across the outlet flow plate using a second pressure transducer. Element 13: wherein directing fluid through a rock core sample includes directing fluid through a rock core sample having a ratio of an inlet primary face surface area ($SA_{IF}$) to a sidewall surface area ($SA_{SW}$) of at least about 1.75. Element 14: wherein directing fluid through a rock core sample includes directing fluid through a rock core sample having a ratio of an inlet primary face surface area ($SA_{IF}$) to a sidewall surface area ($SA_{SW}$) of at least about 3.5. Element 15: wherein directing fluid through a rock core sample includes directing fluid through a rock core sample having a ratio of an inlet primary face surface area ($SA_{IF}$) to a sidewall surface area ($SA_{SW}$) ranging from about 3.5 and about 6.0. Element 16: wherein directing fluid through the rock core sample includes directing fluid through the rock core sample having a diameter (D) and the thickness (T). Element 17: wherein directing fluid through the rock core sample includes directing fluid through the rock core sample having a ratio of the diameter (D) to the thickness (T) of at least 1. Element 18: wherein directing fluid through the rock core sample includes directing fluid through the rock core sample having a ratio of the diameter (D) to the thickness (T) of at least 2. Element 19: wherein directing fluid includes directing a liquid, a gas, or a combination of a liquid and a gas.

Those skilled in the art to which this application relates will appreciate that other and further additions, deletions, substitutions and modifications may be made to the described embodiments.

What is claimed is:

1. A method for testing permeability, comprising:
directing fluid through a rock core sample having an inlet primary face, an outlet primary face and one or more sidewalls having a thickness (T) adjoining the inlet primary face and the outlet primary face, the directing occurring while the sidewalls are unbounded; and
measuring a flow rate of fluid exiting the outlet primary face.

2. The method according to claim 1, wherein directing fluid through a rock core sample includes directing fluid through a rock core sample having a ratio of an inlet primary face surface area ($SA_{IF}$) to a sidewall surface area ($SA_{SW}$) of at least about 0.4.

3. The method according to claim 2, further including placing the rock core sample between an inlet flow plate coupled to the inlet primary face and an outlet flow plate coupled to the outlet primary face prior to directing fluid through the rock core sample.

4. The method according to claim 3, further including forming equipotential boundaries on the inlet primary face and the outlet primary face using the inlet and outlet flow plates.

5. The method according to claim 4, further including creating a fluid potential gradient vector within 10 degrees of perpendicular with the equipotential boundaries.

6. The method according to claim 3, further including directing fluid through a plurality of distribution channels in the inlet flow plate.

7. The method according to claim 6, further including directing fluid through a plurality of concentric axial rings in the inlet flow plate.

8. The method according to claim 7, further including directing fluid through the plurality of concentric axial rings connected by one or more radial paths in the inlet flow plate.

9. The method according to claim 3, further including collecting fluid from a plurality of distribution channels in the outlet flow plate.

10. The method according to claim 9, further including collecting fluid from a plurality of concentric axial rings in the outlet flow plate.

11. The method according to claim 10, further including collecting fluid from the plurality of concentric axial rings connected by one or more radial paths in the outlet flow plate.

12. The method according to claim 3, further including translating a first fluid pressure across the inlet flow plate using a first pressure transducer.

13. The method according to claim 12, further including translating a second pressure across the outlet flow plate using a second pressure transducer.

14. The method according to claim 1, wherein directing fluid through a rock core sample includes directing fluid through a rock core sample having a ratio of an inlet primary face surface area ($SA_{IF}$) to a sidewall surface area ($SA_{SW}$) of at least about 1.75.

15. The method according to claim 1, wherein directing fluid through a rock core sample includes directing fluid through a rock core sample having a ratio of an inlet primary face surface area ($SA_T$) to a sidewall surface area ($SA_{SW}$) of at least about 3.5.

16. The method according to claim 1, wherein directing fluid through a rock core sample includes directing fluid through a rock core sample having a ratio of an inlet primary face surface area ($SA_T$) to a sidewall surface area ($SA_{SW}$) ranging from about 3.5 and about 6.0.

17. The method according to claim 1, wherein directing fluid through the rock core sample includes directing fluid through the rock core sample having a diameter (D) and the thickness (T).

18. The method according to claim 17, wherein directing fluid through the rock core sample includes directing fluid through the rock core sample having a ratio of the diameter (D) to the thickness (T) of at least 1.

19. The method according to claim 17, wherein directing fluid through the rock core sample includes directing fluid through the rock core sample having a ratio of the diameter (D) to the thickness (T) of at least 2.

20. The method according to claim 1, wherein directing fluid includes directing a liquid, a gas, or a combination of a liquid and a gas.

\* \* \* \* \*

UNITED STATES PATENT AND TRADEMARK OFFICE
CERTIFICATE OF CORRECTION

| | | |
|---|---|---|
| PATENT NO. | : 11,119,024 B2 | Page 1 of 1 |
| APPLICATION NO. | : 16/582276 | |
| DATED | : September 14, 2021 | |
| INVENTOR(S) | : Jacob Andrew McGregor | |

It is certified that error appears in the above-identified patent and that said Letters Patent is hereby corrected as shown below:

In the Specification

Column 3, Line 34, after -- A velocity vector -- delete "if $\vec{v}$" and insert -- $\vec{v}$ --

Signed and Sealed this
First Day of March, 2022

Drew Hirshfeld
*Performing the Functions and Duties of the
Under Secretary of Commerce for Intellectual Property and
Director of the United States Patent and Trademark Office*